(12) United States Patent
Perkins et al.

(10) Patent No.: US 12,251,464 B1
(45) Date of Patent: Mar. 18, 2025

(54) COMPOSITIONS AND METHODS FOR SUNLESS TANNING

(71) Applicant: Earth To Malibu, LLC, Alexander City, AL (US)

(72) Inventors: Richard Scott Perkins, Alexander City, AL (US); Michael Stiles, Woodland Hills, CA (US)

( * ) Notice: Subject to any disclaimer, the term of this patent is extended or adjusted under 35 U.S.C. 154(b) by 0 days.

(21) Appl. No.: 18/760,549

(22) Filed: Jul. 1, 2024

Related U.S. Application Data

(63) Continuation-in-part of application No. 18/669,051, filed on May 20, 2024, now abandoned.

(51) Int. Cl.
*A61K 8/97* (2017.01)
*A61K 8/9789* (2017.01)
*A61Q 19/04* (2006.01)

(52) U.S. Cl.
CPC ............ *A61K 8/9789* (2017.08); *A61Q 19/04* (2013.01); *A61K 2800/805* (2013.01)

(58) Field of Classification Search
CPC . A61K 8/9789; A61K 2800/805; A61Q 19/04
See application file for complete search history.

(56) References Cited

U.S. PATENT DOCUMENTS

| | | | |
|---|---|---|---|
| 9,289,375 B2 | 3/2016 | Drapeau et al. | |
| 9,511,034 B1 | 12/2016 | Garrett | |
| 11,833,242 B2 | 12/2023 | Boland et al. | |
| 2019/0224193 A1 | 7/2019 | Reid et al. | |
| 2023/0338455 A1 | 10/2023 | Camussi et al. | |

FOREIGN PATENT DOCUMENTS

| | | |
|---|---|---|
| WO | 2016119911 A1 | 8/2016 |
| WO | 2024031762 A1 | 2/2024 |

OTHER PUBLICATIONS

C. Puglia Et Al., "Protective effect of red orange extract supplementation against UV-induced skin damages: photoaging and solar lentigines", Journal of Cosmetic Dermatology, Jun. 2014, 13, 151-157.
Kathy Ramirez, "Oral Sunscreen Reduces Skin Cancer Risk", Lift Extension Magazine, Jun. 2016.
Saric Et Al., "Systematic Review of Oral and Topical Botanicals in Reducing Photosensitivity", Dermatology, vol. 2, Issue2, 2017, 100DRMTOJ2124.
Wikipedia, "Beta vulgaris", the free encyclopedia, retrieved May 10, 2024.
Wikipedia, "Bixa orellana", the free encyclopedia, retrieved May 20, 2024.
Wikipedia, "Blood orange", the free encyclopedia, retrieved May 10, 2024.
Wikipedia, "Citrus x sinensis", the free encyclopedia, retrieved May 20, 2024.
Wikipedia, "Daucus carota", the free encyclopedia, retrieved May 10, 2024.
Wikipedia, "Infusion", the free encyclopedia, retrieved May 10, 2024.
Wikipedia, "Nicotinamide adenine dinucleotide", the free encyclopedia, retrieved Jun. 21, 2024.
Wikipedia, "Olive", the free encyclopedia, retrieved May 10, 2024.
Wikipedia, "Phlebodium aureum", the free encyclopedia, retrieved Jun. 21, 2024.
Wikipedia, "Rosemary", the free encyclopedia, retrieved May 10, 2024.
Wikipedia, "Saccharina latissima", the free encyclopedia, retrieved May 10, 2024.
Wikipedia, "Sunless tanning", the free encyclopedia, retrieved May 8, 2024.

*Primary Examiner* — Jessica Worsham
(74) *Attorney, Agent, or Firm* — Stonebridge IP, PLLC

(57) ABSTRACT

This disclosure is directed to a composition that includes *Citrus sinensis*, Blood Orange; *Daucus carota*, Carrot; *Beta vulgaris*, Beet; *Curcuma longa*, Turmeric; *Bixa orellana*, Annatto; *Rosmarinus officinalis*, Rosemary; *Saccharina latissima*, Kombu; *Polypodium leucotomos*; Nicotinamide Adenine Dinucleotide, and an oil; and includes methods of making the composition; and methods of using the composition for sunless tanning.

12 Claims, No Drawings

COMPOSITIONS AND METHODS FOR SUNLESS TANNING

RELATED APPLICATIONS

This application claims priority to U.S. application Ser. No. 18/669,051, filed on May 20, 2024, which is herein incorporated by reference in its entirety.

BACKGROUND

Technical Field of the Invention

The field of this invention is directed to sunless-tanning products and skin moisturizing products.

Description of the Related Art

People who suffer from skin problems must be careful about what they put on their skin. Many of these people search for products that are natural. However, in the skin care and cosmetics industry the word "natural" is used loosely and many products that claim to be "natural" include ingredients that are not natural.

Numerous self-tanning products are currently available. All self-tanning products available on the market use either DHA (Dihydroxyacetone) or EPA (Erythrulose). DHA or EPA are in fact not natural ingredients. In 1977, the FDA approved topical application of DHA in self-tanners and bronzers, however, this ingredient is not approved for ingestion, and it is easy to ingest if your eyes and mouth are not properly covered during use. Further, what is put on the skin is ultimately absorbed into the body. Recent research has indicated that dihydroxyacetone (DHA) may cause cell damage via free radical reactions. Research also indicates that free radical reactions can cause the skin to be more susceptible to UV damage.

Accordingly, there is a need in the art for effective, safe, natural ingredient based self-tanning products that can provide the tanning effects consumers desire, and simultaneously provide benefits to the skin.

SUMMARY DISCLOSURE OF THE INVENTION

This disclosure is directed to a composition that includes *Citrus sinensis*, Blood Orange; *Daucus carota*, Carrot; *Beta vulgaris*, Beet; *Curcuma longa*, Turmeric; *Bixa orellana*, Annatto; *Rosmarinus officinalis*, Rosemary; *Saccharina latissima*, Kombu; *Polypodium leucotomos*; Nicotinamide Adenine Dinucleotide; and olive oil, apricot oil, jojoba oil, lavender oil, mango oil, or combinations thereof; and includes methods of making the composition; and methods of using the composition for sunless tanning.

Other features and aspects will be apparent from the following detailed description, the drawings, and the claims.

DETAILED DISCLOSURE OF THE INVENTION

This disclosure is directed to compositions that include *Citrus sinensis*, *Daucus carota*, *Beta vulgaris*, *Curcuma longa*, *Bixa orellana*, *Rosmarinus officinalis*, *Saccharina latissima*, Kombu; *Polypodium leucotomos*; Nicotinamide Adenine Dinucleotide; and olive oil, apricot oil, jojoba oil, lavender oil, mango oil, or combinations thereof.

The following detailed description is provided to assist the reader in gaining a comprehensive understanding of the methods, products, and/or systems described herein. However, various changes, modifications, and equivalents of the methods, products, and/or systems described herein will be apparent to an ordinary skilled artisan.

MODES FOR CARRYING OUT THE INVENTION

In embodiments, the disclosed product is a composition that includes *Citrus sinensis* at about 15% to about 23% by weight of the composition; *Daucus carota* at about 6% to about 10% by weight of the composition; *Beta vulgaris* at about 0.8% to about 1.2% by weight of the composition; *Bixa orellana* at about 1.6% to about 2.4% by weight of the composition; *Rosmarinus officinalis* at about 0.8% to about 1.2% by weight of the composition; *Saccharina latissima* at about 0.8% to about 1.2% by weight of the composition; *Polypodium leucotomos* at about 0.01% to 0.15% by weight of the composition; Nicotinamide Adenine Dinucleotide at about 2% to about 6% by weight of the composition and the oil at about 54% to about 82% by weight of the composition.

In a preferred embodiment, the disclosed product includes *Citrus sinensis*, Blood Orange, at about 19% by weight; *Daucus carota*, Carrot, at about 8% by weight; *Beta vulgaris*, Beet, at about 1% by weight; *Curcuma longa*, Turmeric, at about 1% by weight, *Bixa orellana*, Annatto, at about 2% by weight; *Rosmarinus officinalis*, Rosemary at about 1% by weight; *Saccharina latissima*, Kombu at about 1% by weight; *Polypodium leucotomos* at about 0.1% by weight; Nicotinamide Adenine Dinucleotide at about 4% by weight, and olive oil, apricot oil, jojoba oil, lavender oil, mango oil, or combinations thereof at about 66% by weight of the composition.

The compositions can be in the form of a mousse, spray (for spray tan), stick, milk, tanning waters, lotions, mist, body butter, mud, foam, drops, or towelettes. In addition, a cream, paste, liquid, solid, gel, suspension, dispersion, solid, emulsion, aerosol, powder, tablet, capsule, pill, suspension, dispersion, or emulsion. Also, the compositions disclosed herein can be in a form suitable for dilutions. In one preferred embodiment, the compositions are included in the form of a cream, dispersion, gel, or emulsion suitable to be applied to human skin. The compositions can include carriers, diluents, adjuvants, solubilizing agents, suspending agents, fillers, surfactants, an antimicrobial agent, a preservative, a viscosity modifier, a thixotropy modifier, a wetting agent, an emulsifier, etc. These terms are used consistent with current usage in the pharmaceutical arts as evidenced, for example, by Remington's Pharmaceutical Sciences, Sixteenth Edition, E. W. Martin (Mack Publishing Co., Easton, Pa., 1980); and Remington: Essentials of Pharmaceutics, Pharmaceutical Press; 1st edition (Apr. 1, 2013).

In embodiments, the composition may consist essentially of the above ingredients: *Citrus sinensis*, Blood Orange; *Daucus carota*, Carrot; *Beta vulgaris*, Beet; *Curcuma longa*, Turmeric; *Bixa orellana*, Annatto; *Rosmarinus officinalis*, Rosemary; *Saccharina latissima*, Kombu; *Polypodium leucotomos*; Nicotinamide Adenine Dinucleotide; and olive oil, apricot oil, jojoba oil, lavender oil, mango oil, or combinations thereof. In this case, the composition could include additional additives, for example, for moisturizing, for a body butter, for a bronzer stick, highlighter stick, or an SPF lotion. By way of example, additives could also include ingredients such as Shea butter, candelilla wax, micro crystalline wax, red algae, mica, or zinc oxide, or those mentioned above.

In embodiments, the composition may consist of the above ingredients: *Citrus sinensis*, Blood Orange; *Daucus*

*carota*, Carrot; *Beta vulgaris*, Beet; *Curcuma longa*, Turmeric; *Bixa orellana*, Annatto; *Rosmarinus officinalis*, Rosemary; *Saccharina latissima*, Kombu; *Polypodium leucotomos*; Nicotinamide Adenine Dinucleotide; and olive oil, apricot oil, jojoba oil, lavender oil, mango oil, or combinations thereof. In this case, the compositions would not necessarily exclude common impurities, side products, and the like, that could be present due to the extraction or manufacturing process.

Sunless tanning products commonly include the ingredients dihydroxyacetone (DHA) and EPA (Erythrulose). DHA and EPA are color additives that darken the skin by reacting with amino acids in the skin's surface. In preferred embodiments of this invention, the present compositions do not include DHA or EPA.

Preferred embodiments of the present compositions include Sanguinello. Sanguinello mitigates the effects of UV rays on the skin thereby reducing susceptibility to skin cancer.

The inventive compositions raise the level of melanin, a pigment in the skin, and produce a tanning effect in the epidermis layer of the skin. This is the tanning effect whereby the skin becomes darker in shade due to an increased level of melanin. This is a natural tanning effect and should not be confused with a staining of the skin.

Accordingly, the inventive compositions can be used in methods of sunless tanning including applying a composition of the present disclosure to a subject's skin to produce a tanning effect. The amount applied would be an amount consistent with amounts used when applying moisturizers, tanning lotions, and the like, to the skin. That is, applying an amount sufficient to provide a thin layer of the composition on the subject's skin. The application of the inventive compositions to the skin produces increased levels of melanin in the subject's skin thereby producing a tanning effect. It is noted therefore that the present compositions, in preferred embodiments, do not include any color additives that darken the skin by any other means other than increasing melanin. The compositions, in preferred embodiments, can thus exclude dihydroxyacetone (DHA) and/or Erythrulose (EPA). As noted above, DHA and EPA are color additives that darken the skin by reacting with amino acids in the skin's surface.

In other embodiments, however, the compositions may contain natural ingredients and herbs which contain darker pigments, so as to provide a darker hue upon application. These natural ingredients which contain darker pigments could include various berries, various barks, various leaves, beets, or any other natural constituents for color variation. The process with these ingredients would be extracting the pigment from the herb.

The disclosure further provides methods of making a self-tanning composition including slicing and dehydrating the constituent ingredients blood orange, carrot, beet, turmeric, Annatto, Rosemary, and Kombu; infusing the ingredients into olive oil; allowing the infused olive oil to maturate for about 21 days or more; extracting the constituents from the olive oil and pressing the constituent ingredients thereby producing a concentrated oil. The concentrated oil is then added back to the original olive oil to produce the final product.

Glossary

Sunless tanning, also known as self-tanning, or spray tanning, or fake tanning, refers to obtaining the effect of a suntan without exposure to the Sun. Sunless tanning involves the use of oral agents (carotenoids), or creams, lotions or sprays applied to the skin. Sunless tanning products commonly include the ingredients dihydroxyacetone (DHA) and Erythrulose (EPA). DHA and EPA are color additives that darken the skin by reacting with amino acids in the skin's surface. See Sunless Tanning, Wikipedia, the free encyclopedia, of record.

*Citrus sinensis* is known as a sweet orange. It is a commonly cultivated species of orange that includes Valencia oranges, blood oranges and navel oranges. Blood orange is a variety of oranges with crimson, or blood-colored flesh. It is a sweet orange variety (*Citrus sinensis*) and is also known as raspberry orange or red orange. Sanguinello is a variety of *Citrus sinensis*. See *Citrus* x *sinensis*, Wikipedia, the free encyclopedia, of record; and Blood Orange, Wikipedia, the free encyclopedia, of record.

*Daucus carota* has common names including wild carrot, European wild carrot, bird's nest, bishop's lace, and Queen Anne's lace (North America), is a flowering plant in the family Apiaceae. Domesticated carrots are cultivars of *Daucus carota*, subsp. *sativus*. See *Daucus carota*, Wikipedia, the free encyclopedia, of record.

*Beta vulgaris* (beet) is a species of flowering plant in the subfamily Betoideae of the family Amaranthaceae. See *Beta vulgaris*, Wikipedia, the free encyclopedia, of record.

*Bixa orellana*, also known as achiote, is a shrub or small tree and is known as the source of annatto, a natural orange-red condiment obtained from waxy arils that cover its seeds. See *Bixa orellana*, Wikipedia, the free encyclopedia, of record.

*Rosmarinus officinalis*, also known as rosemary, is a shrub with fragrant, evergreen, needle-like leaves and white, pink, purple, or blue flowers. See Rosemary, Wikipedia, the free encyclopedia, of record.

*Saccharina latissima* is a brown alga of the family Laminariaceae. See *Saccharina latissima*, Wikipedia, the free encyclopedia, of record.

*Olea europaea* is a species of small tree or shrub in the family Oleaceae. See Olive, Wikipedia, the free encyclopedia, of record. In embodiments of the invention, *Olea europaea* is olive oil.

*Polypodium leucotomos* is a species of fern in the family of Polypodiacae. The South American Polydium leucotomos is known locally as "calaguala," and extracts of this fern are called "anapsos." See *Phlebodium aureum*, Wikipedia, the free encyclopedia, of record.

Nicotinamide Adenine Dinucleotide is a coenzyme central to metabolism. Found in all living cells, NAD is called a dinucleotide because it consists of two nucleotides joined through their phosphate groups. See Nicotinamide adenine dinucleotide, Wikipedia, the free encyclopedia, of record.

Apricot oil can refer to apricot seed oil or apricot kernel oil.

Infusion is a process of extracting chemical compounds or flavors from plant material in a solvent such as water, oil, or alcohol, by allowing the material to remain suspended in the solvent over time. See infusion, Wikipedia, the free encyclopedia, of record.

EXAMPLE 1

This Example shows an exemplary method of making the compositions.

The seven starting ingredients: Blood Orange, Carrot, Beet, Turmeric, Annatto, Rosemary, and Kombu, each need to be fresh and organic. In this example, the Blood Orange is 78 g. The Carrot is 32 g; the Beet is 3 g; the Turmeric is 3 g; the Annatto is 7 g; the Rosemary is 3 g; the Kombu is 3 g; and the Olive Oil is 300 ml.

Each of these Ingredients is then sliced and dehydrated. All seven ingredients are then infused into Olive Oil and allowed to maturate for a minimum period of 21 days to provide the requisite maturation. The constituents are then extracted from the original olive oil and pressed. When the constituents are pressed, a concentrated oil is produced. This concentrated oil from the pressed constituents is then added back into the original olive oil. The product is produced in liquid form and the quantity in this example is around 10.0 oz to about 10.5 oz or about 300 ml.

The room temperature should be between about 66 degrees Fahrenheit and about 73 degrees Fahrenheit. The Preferred Range of Ingredient Measurements is about +/−5% to about 7% for the above or about +/−20% generally. This will vary based on the size of the batch.

Additives can be added to the final product as follows to make a tanner or self-tanner in the form of a moisturizer, a body butter, a bronzer stick, a highlighter stick, or an SPF (Sun Protection Factor) Lotion. In this example, use 45 ml or 1.522 ounces of the final product per about 10.0 oz to about 10.5 oz of Additive. Mix the product into the additive using a professional grade mixer so that the product is thoroughly integrated into the additive and the desired texture is achieved.

Additives include, but are not limited to, for a moisturizer: apricot oil, i.e., apricot seed oil or apricot kernel oil, Shea butter. For body butter: Jojoba Oil or Shea Butter. For a bronze stick: Candelilla Wax or Red Algae. For a Highlighter Stick: Microcrystalline Wax or Mica. For an SPF Lotion: zinc oxide, lavender oil, or mango oil.

EXAMPLE 2

This Example shows another exemplary method of making the compositions.

The nine starting ingredients: Blood Orange, Carrot, Beet, Turmeric, Annatto, Rosemary, and Kombu, each need to be fresh and organic. In this example, the Blood Orange is 78 g (about 19%), the Carrot is 32 g (about 8%); the Beet is 3 g (about 1%); the Turmeric is 3 g (about 1%); the Annatto is 7 g (about 2%); the Rosemary is 3 g (about 1%); the Kombuis 3 g (about 1%); the *Polypodium leucotomos* is 120-320 mg, the Nicotinamide Adenine Dinucleotide is 15 g (about 4%), and the Olive Oil is 300 ml (about 66%). All percentages by weight.

Each of these Ingredients is then sliced and dehydrated, with the exception of the Nicotinamide Adenine Dinucleotide, which is in powder form and thus does not need to be sliced, but it is dehydrated. All nine ingredients are then infused into Olive Oil and allowed to maturate for a minimum period of 21 days to provide the requisite maturation. The constituents are then extracted from the original olive oil and pressed. When the constituents are pressed, a concentrated oil is produced. This concentrated oil from the pressed constituents is then added back into the original olive oil. The product is produced in liquid form and the quantity in this example is around 10.0 oz to about 10.5 oz or about 300 ml.

The room temperature should be between about 66 degrees Fahrenheit and about 73 degrees Fahrenheit. The Preferred Range of Ingredient Measurements is about +/−5% to about 7% for the above, or about +/−20% generally. This will vary based on the size of the batch.

Additives can be added to the final product as follows to make a tanner or self-tanner in the form of a moisturizer, a body butter, a bronzer stick, a highlighter stick, or an SPF (Sun Protection Factor) Lotion. In this example, use 45 ml or 1.522 ounces of the final product per about 10.0 oz to about 10.5 oz of Additive. Mix the product into the additive using a professional grade mixer so that the product is thoroughly integrated into the additive and the desired texture is achieved.

Additives include, but are not limited to, for a moisturizer: apricot oil, i.e., apricot seed oil or apricot kernel oil, Shea butter. For body butter: Jojoba Oil or Shea Butter. For a bronze stick: Candelilla Wax or Red Algae. For a Highlighter Stick: Microcrystalline Wax or Mica. For an SPF Lotion: zinc oxide, lavender oil, or mango oil.

While this disclosure includes specific examples, it will be apparent after an understanding of the disclosure of this application has been attained that various changes in form and details may be made in these examples without departing from the spirit and scope of the claims and their equivalents.

The invention claimed is:

1. A sunless-tanning composition comprising: extract of *Citrus sinensis*, an extract of *Daucus carota*, an extract of *Beta vulgaris*, an extract of *Curcuma longa*, an extract of *Bixa orellana*, an extract of *Rosmarinus officinalis*, a *Saccharina latissima* extract; an extract of *Polypodium leucotomos*; and a Nicotinamide Adenine Dinucleotide powder; and an oil comprising: olive oil, apricot oil, jojoba oil, lavender oil, mango oil, or combinations thereof.

2. The sunless-tanning composition of claim 1, wherein the extract of *Citrus sinensis* comprises Sanguinello.

3. The sunless-tanning composition of claim 1, wherein the oil comprises olive oil.

4. The sunless-tanning composition of claim 1, wherein the extract of *Citrus sinensis* is about 15% to about 23% by weight of the composition; the extract of *Daucus carota* is about 6% to about 10% by weight of the composition; the extract of *Beta vulgaris* is about 0.8% to about 1.2% by weight of the composition; the extract of *Curcuma longa* is about 0.8% to about 1.2% by weight of the composition; the extract of *Bixa orellana* is about 1.6% to about 2.4% by weight of the composition; the extract of *Rosmarinus officinalis* is about 0.8% to about 1.2% by weight of the composition; the *Saccharina latissima* extract is about 0.8% to about 1.2% by weight of the composition; the extract of *Polypodium leucotomos* is about 0.01% to 0.15% by weight of the composition; the Nicotinamide Adenine Dinucleotide powder is about 2% to about 6% by weight of the composition and the oil is about 54% to about 82% by weight of the composition.

5. The sunless-tanning composition of claim 4, wherein the extract of *Citrus sinensis* comprises Sanguinello.

6. The sunless-tanning composition of claim 1, wherein the extract of *Citrus sinensis* is about 19% by weight of the composition; the extract of *Daucus carota* is about 8% by weight of the composition; the extract of *Beta vulgaris* is about 1% by weight of the composition; the extract of *Curcuma longa* is about 1% by weight of the composition; the extract of *Bixa orellana* is about 2% by weight of the composition; the extract of *Rosmarinus officinalis* is about 1% by weight of the composition; the *Saccharina latissima* extract is about 1% by weight of the composition; the extract of *Polypodium leucotomos* is about 0.1% by weight of the composition, the Nicotinamide Adenine Dinucleotide powder is about 4% by weight of the composition and the oil is about 66% by weight of the composition.

7. The sunless-tanning composition of claim 6, wherein the extract of *Citrus sinensis* comprises Sanguinello.

8. A method of sunless tanning comprising: applying the composition of claim 1 to human skin, wherein the amount of melanin in the skin is thereby increased.

9. The method of claim 8, wherein the extract of *Citrus sinensis* comprises Sanguinello.

10. A method of making a composition of claim 1 comprising:

dehydrating blood orange, carrot, *Beta vulgaris, Curcuma longa, Bixa orellana, Rosmarinus officinalis, Saccharina latissima*, and *Polypodium leucotomos*;

infusing the dehydrated blood orange, carrot, *Beta vulgaris, Curcuma longa, Bixa orellana, Rosmarinus officinalis, Saccharina latissima, Polypodium leucotomos*; and Nicotinamide Adenine Dinucleotide powder, into an oil selected from the group consisting of: olive oil, apricot oil, jojoba oil, lavender oil, mango oil, and combinations thereof, for 21 days or more to produce an infused oil;

recovering a maturated blood orange, carrot, *Beta vulgaris, Curcuma longa, Bixa orellana, Rosmarinus officinalis, Saccharina latissima, Polypodium leucotomos*, and Nicotinamide Adenine Dinucleotide powder from the infused oil;

pressing the recovered blood orange, carrot, *Beta vulgaris, Curcuma longa, Bixa orellana, Rosmarinus officinalis, Saccharina latissima, Polypodium leucotomos*, and Nicotinamide Adenine Dinucleotide powder to produce a concentrated oil;

adding the concentrated oil back into the infused oil.

11. The method of claim 10, wherein the extract of *Citrus sinensis* comprises Sanguinello.

12. The method of claim 10, wherein the oil comprises olive oil.

* * * * *